US008016836B2

(12) United States Patent
Corrao et al.

(10) Patent No.: US 8,016,836 B2
(45) Date of Patent: Sep. 13, 2011

(54) BONE SCREW DRIVER

(75) Inventors: Ernie Corrao, Bethel, CT (US); Rebecca H. Wahl, Escondido, CA (US); Louise M. Focht, Del Mar, CA (US)

(73) Assignee: Tornier, Inc., Edina, MN (US)

( * ) Notice: Subject to any disclaimer, the term of this patent is extended or adjusted under 35 U.S.C. 154(b) by 627 days.

(21) Appl. No.: 11/820,597

(22) Filed: Jun. 19, 2007

(65) Prior Publication Data
US 2008/0319450 A1 Dec. 25, 2008

(51) Int. Cl.
*A61B 17/58* (2006.01)
(52) U.S. Cl. .................. 606/104; 411/2; 81/453
(58) Field of Classification Search .......... 606/104; 81/453; 411/2–7, 39, 410
See application file for complete search history.

(56) References Cited

U.S. PATENT DOCUMENTS

| 1,562,543 | A | * | 11/1925 | Cox | 81/453 |
|---|---|---|---|---|---|
| 3,604,487 | A | * | 9/1971 | Gilbert | 81/443 |
| 5,484,440 | A | * | 1/1996 | Allard | 606/916 |
| 5,971,987 | A | * | 10/1999 | Huxel et al. | 606/916 |
| 6,755,836 | B1 | * | 6/2004 | Lewis | 606/916 |
| 7,174,812 | B1 | * | 2/2007 | Chiang | 81/125 |
| 7,226,453 | B2 | * | 6/2007 | Chao et al. | 606/104 |
| 2004/0068269 | A1 | * | 4/2004 | Bonati et al. | 606/104 |
| 2004/0133207 | A1 | * | 7/2004 | Abdou | 606/73 |
| 2007/0106283 | A1 | * | 5/2007 | Garcia et al. | 606/1 |

OTHER PUBLICATIONS

Newdeal Spin Snap-Off Screw Brochure. Copyright 2005 Integra LifeSciences Corporation. The Applicants admit that this brochure is prior art.
DePuy FRS™—Fusion and Reconstruction System, © DePuy, a Johnson & Johnson company 2005-2006.

* cited by examiner

*Primary Examiner* — Thomas C Barrett
*Assistant Examiner* — Christian Sevilla
(74) *Attorney, Agent, or Firm* — Faegre & Benson LLP

(57) ABSTRACT

A bone screw driver (12) for inserting a bone screw (14) into a bone region (218A) includes a driver shaft (12B) that selectively engages the bone screw (14). The bone screw (14) includes a screw threaded region (14A) and a screw engagement region (14B). The screw engagement region (14B) includes a screw shaft (14D) and an engager ring (14E). The driver shaft (12B) includes a shaft aperture (322), a first resilient member (324A), and a first shaft projection (326A). The shaft aperture (322) receives at least a portion of the screw shaft (14D), the first resilient member (324A) engages the screw shaft (14D) to inhibit movement of the screw shaft (14D), and the first shaft projection (326A) engages the engager ring (14E) so that rotation of the driver shaft (12B) results in rotation of the bone screw (14). With this design, in certain embodiments, the bone screw (14) can be removed with the bone screw driver (12) from a screw retainer (16) that retains the bone screw (14), and inserted into the bone region (218A) without the physician contacting with the bone screw (14). This reduces the likelihood of contaminating the bone screw (14) and increases the likelihood of success for the procedure.

10 Claims, 4 Drawing Sheets

BONE SCREW DRIVER

BACKGROUND

It is often necessary to fuse two bone regions together to repair a fracture or to fuse a joint. One type of device used to fuse two bone regions is a bone screw than is threaded into the bone regions with a bone screw driver by a physician. Because the size and orientation of the bone regions that need to be fused can vary greatly, the bone screws are designed in varying lengths and diameters. For any particular bone fusing procedure, the size of the bone screw must be chosen properly so as to maximize the stability of the bone regions after they are fused together, and to minimize the irritation adjacent to the area where the bone screw has been inserted.

Often the physician is provided with a container that contains a plurality of alternatively sized bone screws. With this system, the physician can select the bone screw from the container that is appropriate for the procedure being performed.

It should be noted that it is important to keep the bone screw sterile. Accordingly, it is desired to minimize human contact with the bone screw prior to insertion into the bone regions.

SUMMARY

The present invention is directed toward a bone screw driver for inserting a bone screw into a bone region. The bone screw includes a screw threaded region and a screw engagement region. The screw engagement region includes a screw shaft and an engager ring. The bone screw driver includes a driver handle and a driver shaft that is coupled to the driver handle. The driver shaft includes a shaft aperture, a first resilient member, and a first shaft projection. The shaft aperture receives at least a portion of the screw shaft, the first resilient member engages the screw shaft to inhibit movement of the screw shaft, and the first shaft projection engages the engager ring so that rotation of the driver shaft results in rotation of the bone screw. With this design, in certain embodiments, the bone screw can be removed with the bone screw driver from a screw retainer that contains the bone screw, and inserted into the bone region without the physician directly contacting the bone screw. This reduces the likelihood of contaminating the bone screw and increases the likelihood of success for the procedure.

In one embodiment, the first resilient member extends into the shaft aperture to contact the screw shaft. For example, the first resilient member can cantilever into the shaft aperture to contact the screw shaft. Additionally, the driver shaft can include a second resilient member that extends into the shaft aperture to contact the screw shaft.

Further, in one embodiment, the driver shaft includes a second shaft projection and a third shaft projection that engage the engager ring so that rotation of the driver shaft results in rotation of the bone screw.

Additionally, the present invention is directed to a combination that includes a one or more bone screws, a screw retainer that retains the one or more bone screws, and a bone screw driver as detailed above.

Moreover, the present invention is directed to a method for inserting a bone screw into a bone region. The method including the steps of engaging the bone screw with the driver shaft and rotating the driver shaft and the bone screw to thread the bone screw into the bone region. In this design, the driver shaft can have similar features as detailed above.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
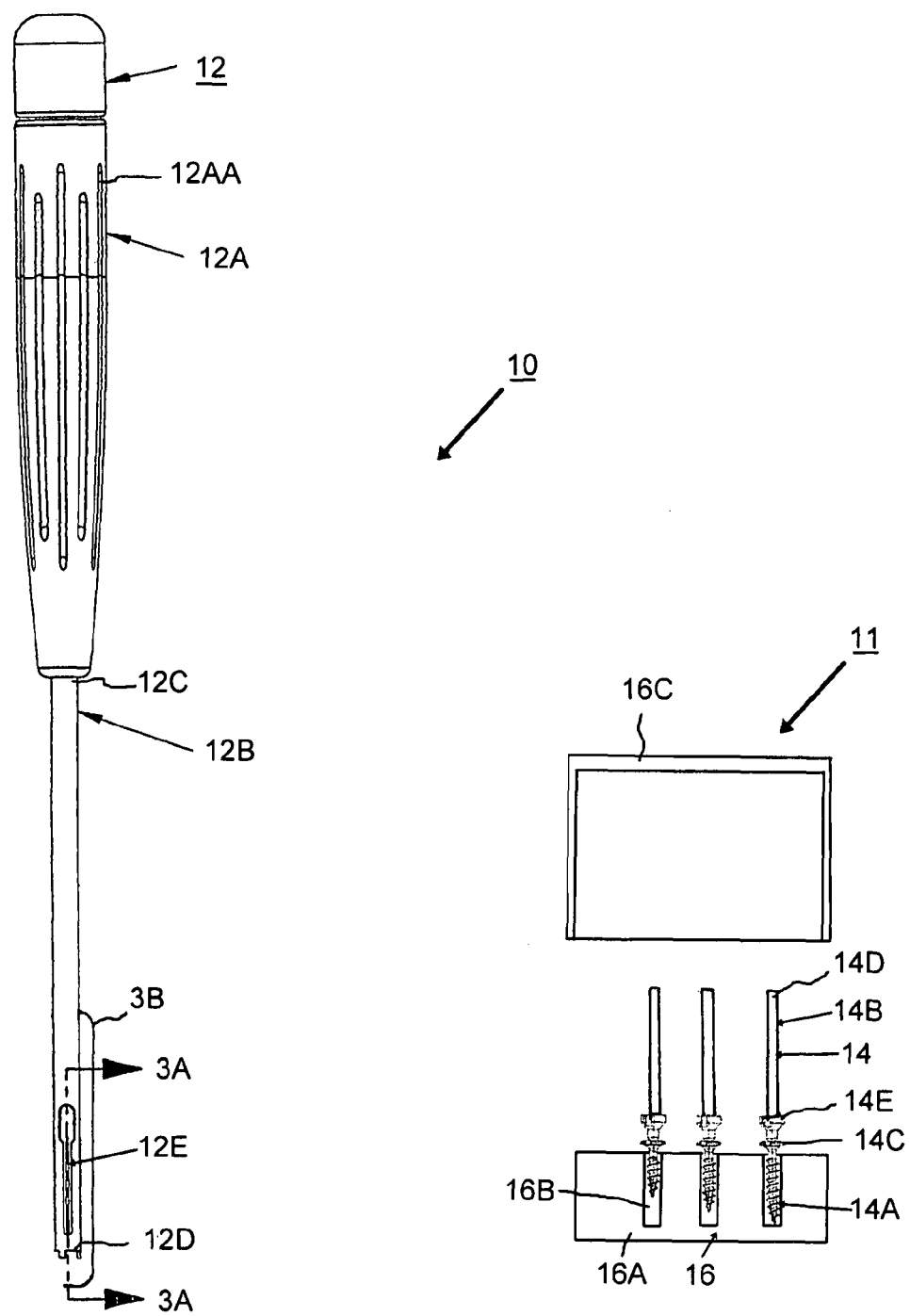
FIG. 1 is a simplified side view of a bone screw assembly in partial cut-away and a bone screw driver having features of the present invention.

FIG. 1 illustrates a combination 10 including a bone screw assembly 11 and a bone screw driver 12 having features of the present invention. The bone screw assembly 11 includes one or more bone screws 14 and a screw retainer 16 that retains the one or more bone screws 14. As an overview, in certain embodiments, the bone screw driver 12 can be used by a physician (not shown) to remove one of the bone screw 14 from the screw retainer 16, and insert the bone screw 14 into one or more bone regions 218A, 218B (illustrated in FIG. 2A) without the physician directly contacting the bone screw 14. This reduces the likelihood of contaminating the bone screw 14 and increases the likelihood of success for the procedure.

The number and design of the bone screws 14 in the bone screw assembly 11 can be varied to achieve the desired range of surgery options. In FIG. 1, the bone screw assembly 11 includes three, bone screws 14. Alternatively, the bone screw assembly 11 could have more than three or less than three bone screws 14. Typically, the number of alternatively sized bone screws 14 is greater than three so that the physician has a large choice of possible bone screws 14 for the procedure.

In FIG. 1, each of the bone screws 14 includes a screw threaded region 14A, and a screw engagement region 14B. The screw threaded region 14A is threaded into one or more of the bone regions 218A, 218B, and the screw engagement region 14B is engaged by the bone screw driver 12 to rotate the bone screw 14 during insertion of the screw threaded region 14A into one or more of the bone regions 218A, 218B. The design and size of the screw threaded region 14A and the screw engagement region 14B of each bone screw 14 can vary according to the desired use for the bone screw assembly 11. In FIG. 1, each of the screw threaded regions 14A has a somewhat similar thread pattern and a different thread length. With this design, the physician can select the bone screw 14 with the desired thread length for the operation. Alternatively, the thread pitch, width or design can be different for each of the bone screws 14.

Additionally, in FIG. 1, each of the screw threaded regions 14A includes a screw head 14C that engages one of the bone regions 218A, 218B when the bone screw 14 is fully inserted.

Further, in FIG. 1, the screw engagement region 14B for each of the bone screws 14 is substantially similar. In this embodiment, the screw engagement region 14B includes a screw shaft 14D and an engager ring 14E. The shaft 14D is engaged by the bone screw driver 12 to retain the bone screw 14 during removal from the screw retainer 16 and insertion into the bone regions 218A, 218B, while the engager ring 14E is engaged by the bone screw driver 12 to rotate the bone screw 14.

In FIG. 1, the shaft 14D has generally right cylindrical shape and has a generally circular cross-section. Alternatively, the shaft 14D can have another configuration. For example, the shaft 14D can have an octagonal or rectangular shaped cross-section.

Further, in FIG. 1, the engager ring 14E is somewhat disk shaped and is located near the screw threaded region 14A. The engager ring 14E is described in more detail below.

The type of material utilized in the bone screws 14 can be varied to meet the requirements of the one or more bone regions 218A, 218B. For example, the bone screws 14 can be formed from titanium, stainless steel, or a bio-absorbable material.

The length and cross-section of screw threaded regions 14A and the screw engagement regions 14B can be varied to suit the procedure being performed on the patient. In one non-exclusive embodiment, the screw threaded regions 14A has a length of between approximately eleven and seventeen millimeters, and the screw engagement region 14B has a length of between approximately ten and twenty millimeters. However, greater or lesser lengths can be utilized.

The screw retainer 16 retains the bone screws 14 prior to the particular bone screw 14 being selected by the physician. In FIG. 1, the screw retainer 16 is designed to retain three, bone screws 14 and includes a retainer base 16A having three screw receivers 16B, e.g. apertures, that retain the bone screws 14 in a spaced apart configuration. Alternatively, the screw retainer 16 could be designed to retain more than three or less than three bone screws 14.

In FIG. 1, the retainer base 16A retains the bone screws 14 with the screw engagement region 14B exposed so that the screw engagement region 14B can be accessed with the bone screw driver 12. With this design, the bone screw driver 12 can be used by the physician to remove the appropriate bone screw 14 from the screw retainer 16, without the physician directly contacting with the bone screw 14.

In one embodiment, the screw retainer 16 maintains the bone screws 14 in a sterile environment. For example, the screw retainer 16 can include a removable, retainer top 16C that can be secured to the retainer base 16A to fully enclose the bone screws 14 in the screw retainer 16.

The bone screw driver 12 selectively retains the selected bone screw 14 so that the bone screw driver 12 can be used to remove the selected bone screw 14 from the screw retainer 16 and so that the bone screw driver 12 can be used to thread the selected bone screw 14 in the bone regions 218A, 218B. In FIG. 1, the bone screw driver 12 includes a handle 12A and a driver shaft 12B that is secured to the handle 12A so that rotation of the handle 12A results in rotation of the driver shaft 12B.

In this embodiment, the handle 12A is sized and shaped to be moved and rotated with a hand of the physician. In FIG. 1, the handle 12A is generally cylindrical shaded and is shaped somewhat similar to the handle of a screwdriver. The handle 12A can include a plurality of handle slots 12AA to facilitate gripping of the handle 12A with the human hand. Alternatively, for example, the handle 12A can have a "T" shaped configuration.

Suitable materials for the handle 12A include plastic (e.g. polyphenylsulfone sold under the trademark Radel), and metal such as aluminum or stainless steel. In one embodiment, the handle 12A is molded onto a portion of the driver shaft 12B. Alternatively, the handle 12A can be secured with an adhesive or pinned mechanically to the driver shaft 12B.

The driver shaft 12B is generally rigid and includes a proximal end 12C that is secured to the handle 12A, an opposed distal end 12D, and a screw engager assembly 12E located near the distal end 12D that engages the screw engagement region 14B of the selected bone screw 14. In FIG. 1, the driver shaft 12B has a generally cylindrical shaped and a generally circular cross-section. Alternatively, the driver shaft 12B can have another configuration. For example, the driver shaft 12B can have an octagonal or rectangular shaped cross-section.

In one embodiment, the driver shaft 12B is integrally formed as a unitary structure. Alternatively, portions of the driver shaft 12B can separately formed and joined together during manufacturing. A non-exclusive example of a suitable material for the driver shaft 12B is stainless steel. In one non-exclusive embodiment, the driver shaft 12B extends approximately 3.5 inches below the handle 12A.

The screw engager assembly 12E is designed to engage the bone screw 14 to facilitate removal of the selected bone screw 14 from the screw retainer 16 and insertion of the bone screw 14 in the patient. With this design, the physician can use the bone screw driver 12 to remove the appropriate bone screw 14 from the screw retainer 16, and insert the bone screw 14 into one or more bone regions 218A, 218B without the physician directly contacting with the bone screw 14. The screw engager assembly 12E is discussed in more detail below.

Figure 2A:
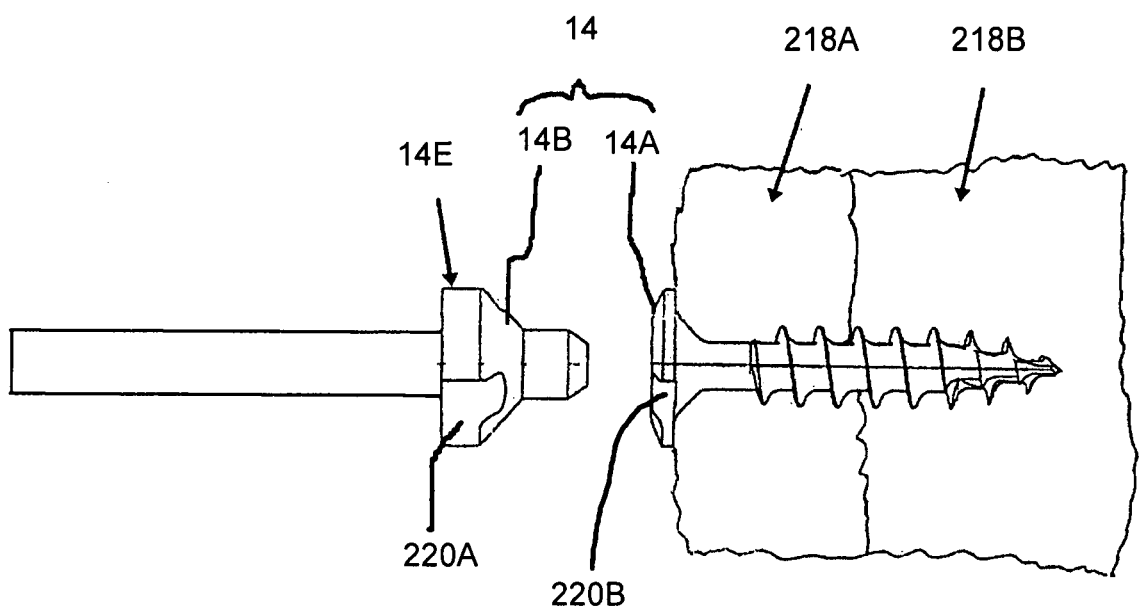
FIG. 2A is a simplified side view of a pair of bone regions, in cut-away, that are fused together with a snap-off bone screw in a decoupled configuration.

FIG. 2A is a simplified side illustration of a bone screw 14 that has been inserted into a first bone region 218A and a second bone region 218B of a human. In this embodiment, the bone screw 14 urges the bone regions 218A, 218B together so that the bone regions 218A, 218B are fused together. The type and location of the bone regions 218A, 218B urged together can vary. For example, the bone screw 14 can be used to fuse a fracture of a human bone, to immobilize and fuse a human joint, or to fuse together adjacent bones. Alternatively, for example, one or more of the bone screws 14 can be used to secure a plate (not shown) or other device to one or more bone regions 218A, 218B.

Additionally, FIG. 2A illustrates that the bone screw 14 is a snap-off type screw, in which the screw engagement region 14B is designed to break away from the screw threaded region 14A after the screw threaded region 14A has been threaded into the bone regions 218A, 218B. Alternatively, the bone screw 14 could have a different design.

It should be noted that in certain embodiments, the bone screw driver 12 (illustrated in FIG. 1) continues to retain the screw engagement region 14B after the screw engagement region 14B has broken away from the screw threaded region 14A. This reduces the likelihood that the screw engagement region 14B will be misplaced.

It should be noted that the bone screw 14 can be inserted with a pilot hole (not shown) or without a pilot hole, depending upon the condition and type of the one or more bone regions 218A, 218B. In one embodiment, the bone screw 14 is self drilling and/or tapping.

Figure 2B:
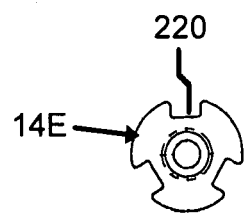
FIG. 2B is a simplified top view of the bone screw of FIG. 2A.

FIGS. 2A and 2B illustrate the engager ring 14E in more detail. The design of the engager ring 14E can be varied to achieve the desired area to be engaged by the bone screw driver 12. In FIGS. 2A and 2B, the engager ring 14E is somewhat cylindrical disk shaped and includes a plurality of spaced apart, circumferentially distributed ring notches 220A. The ring notches 220A allow for engagement by the screw engager assembly 12E of the bone screw driver 12 so that rotation of the bone screw driver 12 results in rotation of the bone screw 14. In FIGS. 2A and 2B, the engager ring 14E includes three spaced apart ring notches 220A that are approximately 120 degrees apart. Alternatively, the engager ring 14E can be designed to have more than three or less than three ring notches 220A. Alternatively, the engager ring 14E can have another configuration. For example, the edges of the ring notches 220A can be rounded to be more tissue friendly.

Additionally, the screw threaded region 14A can include a head that is somewhat cylindrical disk shaped and includes a plurality of spaced apart, circumferentially distributed head notches 220B. The ring notches 220B allow for engagement by the screw engager assembly 12E of the bone screw driver 12 so that the screw threaded region 14A can be further inserted or removed after the screw engagement region 14B has broken away from the screw threaded region 14A. In FIG. 2A, the head includes three spaced apart head notches 220B that are approximately 120 degrees apart. Alternatively, the head can be designed to have more than three or less than three head notches 220B.

Figure 3A:
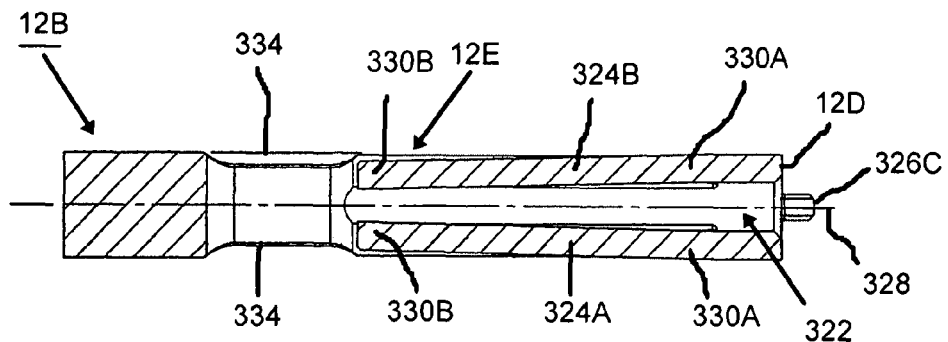
FIG. 3A is a cut-away view taken on line 3A-3A in FIG. 1.
Figure 3B:
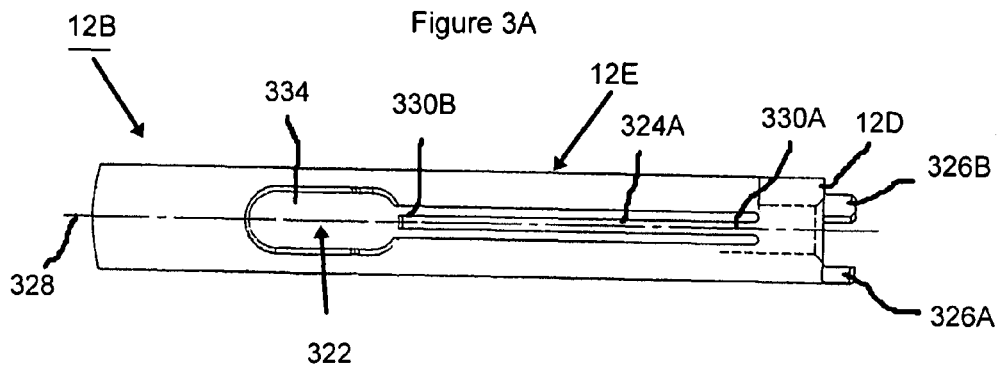
FIG. 3B is an enlarged view of a portion of the bone screw driver taken from FIG. 1.

FIG. 3A is a cut-away view and 3B is a side view of the screw engager assembly 12E of the driver shaft 12B. In this embodiment, the driver shaft 12B includes a shaft aperture 322, a first resilient member 324A, a second resilient member 324B, a first shaft projection 326A, a second shaft projection 326B, and a third shaft projection 326C that cooperate to form the screw engager assembly 12E. Alternatively, the screw engager assembly 12E can have an alternative configuration. For example, the screw engager assembly 12E can have more than two or fewer than two resilient members 324A, 324B, and/or more than three or fewer than three shaft projections 326A, 326B, 326C The shaft aperture 322 receives at least a portion of the screw shaft 14D (illustrated in FIG. 1). In FIGS. 3A and 3B, the shaft aperture 322 is a generally cylindrical shaped opening that extends into a portion of the driver shaft 12B from the distal end 12D along a longitudinal axis 328 of the driver shaft 12B. In one embodiment, the shaft aperture 322 has a diameter that is slightly greater than the diameter of the screw shaft 14D. In one non-exclusive embodiment, the shaft aperture 322 has an aperture depth of between approximately eleven and twelve centimeters.

The resilient members 324A, 324B engage the side of the screw shaft 14D when the screw shaft 14D is inserted into the shaft aperture 322 to inhibit movement of the screw shaft 14D from the shaft aperture 322. In FIGS. 3A, and 3B, each of the resilient members 324A, 324B is a generally rectangular shaped beam that extends into the shaft aperture 322 to contact the screw shaft 14D. For example, each of the beams 324A, 324B can cantilever into the shaft aperture 322 to contact the side of the screw shaft 14D. In this embodiment, each of the beams 324A, 324B includes an attached end 330A that is attached to the rest of the driver shaft 12B near the distal end 12D, and a cantilevering end 330B that cantilevers into the shaft aperture 322. In one embodiment, the beams 324A, 324B are formed by cutting slots 332 in the driver shaft 12B to form the beams 324A, 324B and subsequently deforming the beams 324A, 324B to cantilever inward.

In FIGS. 3A and 3B, the distance between the cantilevering ends 330B is less than the diameter of the shaft aperture 322 and the diameter of the screw shaft 14D. As a result thereof, the cantilevering ends 330B engage the sides of the screw shaft 14D when the screw shaft 14D is inserted into the shaft aperture 322, and the friction between the cantilevering ends 330B and the screw shaft 14D inhibit the screw shaft 14D from being removed from the shaft aperture 322.

Alternatively, one or more of the resilient members 324A, 324B can have a design that is different than that illustrated herein. For example, one or more of the resilient members 324A, 324B can be a spring positioned in the shaft aperture 322 that extends inward.

Additionally, the driver shaft 12B can include one or more side apertures 334 that facilitate manufacturing of the driver shaft 12B.

Figure 3C:
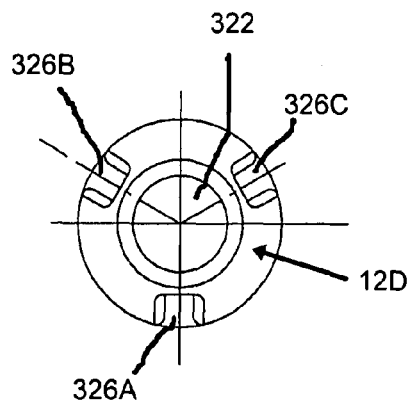
FIG. 3C is an end view of the portion of the bone screw driver of FIG. 3B.
Figure 3D:
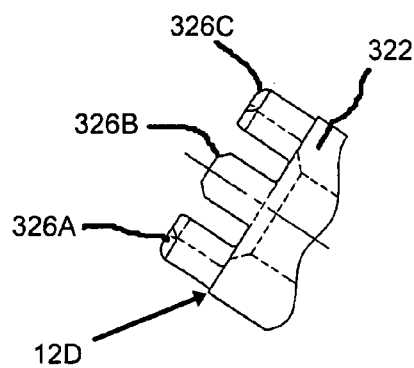
FIG. 3D is a perspective view of the end of the bone screw driver.

The shaft projections 326A, 326B, 326C engage the notches 220 (illustrated in FIG. 2B) of the engager ring 14E (illustrated in FIG. 2B) so that rotation of the driver shaft 12B results in rotation of the bone screw 14. The design of the shaft projections 326A, 326B, 326C can vary according to the design of the notches 220. FIGS. 3C and 3D illustrate the shaft projections 326A, 326B, 326C in more detail. In this embodiment, each of shaft projections 326A, 326B, 326C is a generally rectangular beam with tapered edges, that cantilevers away from the distal end 12D. Further, the spaced apart shaft projections 326A, 326B, 326C are distributed circumferentially and are positioned around the opening to the shaft aperture 322 at approximately 120 degrees relative to each other.

In one non-exclusive embodiment, each of the shaft projections 326A, 326B, 326C extends between approximately 1 and 1.5 millimeters.

As stated above, the bone screw driver 12 can be used by a physician to remove one of the bone screws 14 from the screw retainer 16, and insert the bone screw 14 into one or more bone regions 218A, 218B without the physician directly contacting with the bone screw 14. More specifically, after the physician determines the appropriate bone screw 14, the physician moves the bone screw driver 12 so that the shaft aperture 322 receives the screw shaft 14D. Further, the bone screw driver 12 is moved downward and rotated until the shaft projections 326A, 326B, 326C are positioned in the notches 220. In this position, the resilient members 324A, 324B engage the side of the screw shaft 14D and the shaft projections 326A, 326B, 326C engage the notches 220. As a result thereof, the bone screw driver 12 can be used by a physician to remove the bone screw 14 from the screw retainer 16, and insert the bone screw 14 into one or more bone regions 218A, 218B. Stated in another fashion, the user can easily couple the bone screw driver 12 to the desired bone screw 14, with one hand, without the need of touching or otherwise handling the individual bone screw 14. This feature enables the user to maintain the screw 14 in the most clean and sterile condition possible before inserting the screw 14.

Figure 4:
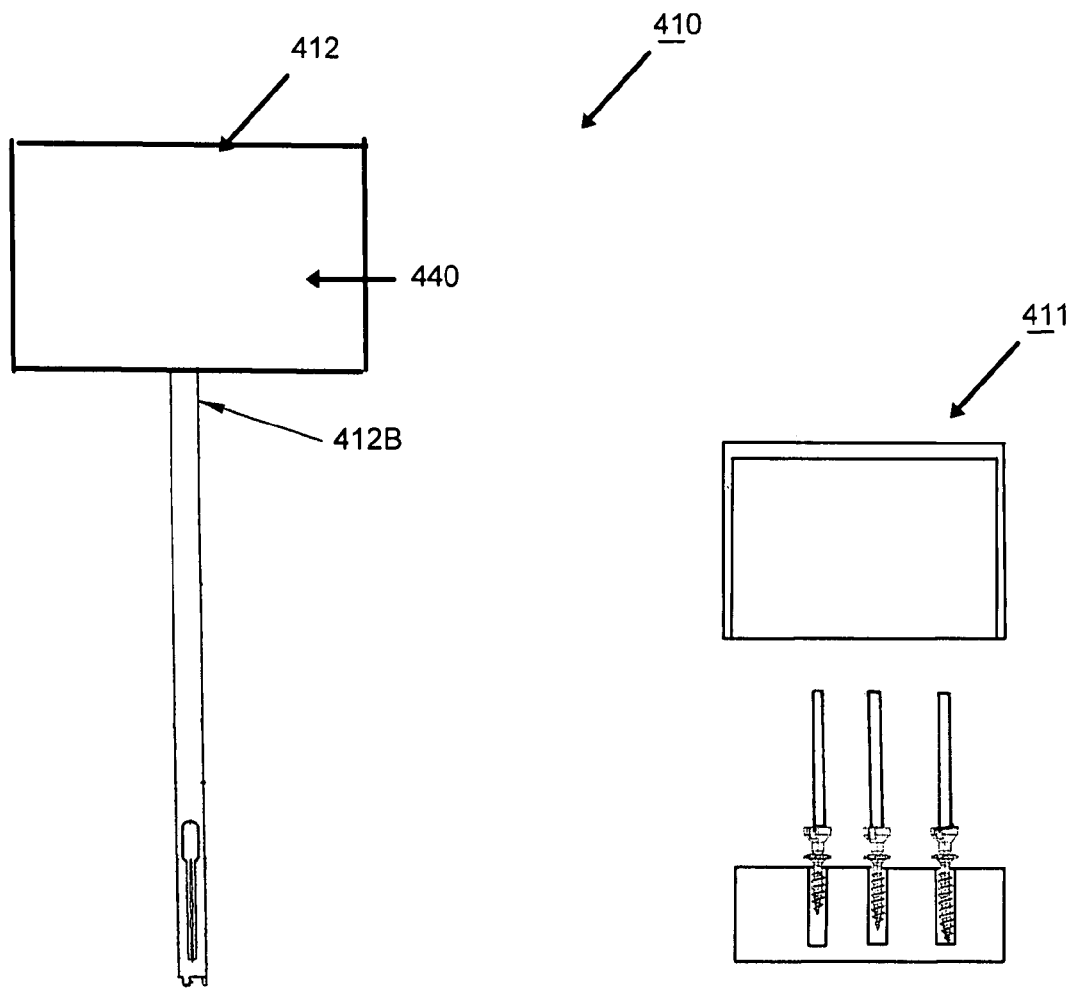
FIG. 4 is a simplified side view of the bone screw assembly in partial cut-away and another embodiment of a bone screw driver having features of the present invention.

FIG. 4 illustrates another embodiment of a combination 410 including a bone screw assembly 411 and a bone screw driver 412 that are somewhat similar to the bone screw driver 12 described above. However, in this embodiment, the bone screw driver 412 includes an electric motor 440 instead of a handle 12A (illustrated in FIG. 1) to electrically rotate the driver shaft 412B.

While the bone screw driver 12, as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:
1. A bone screw driver for inserting a bone screw into a bone region, the bone screw including a screw threaded region and a screw engagement region, the screw engagement region including a screw shaft and an engager ring, the bone screw driver comprising:
   a driver handle;

a driver shaft coupled to the driver handle, the driver shaft including a shaft aperture for receiving at least a portion of the screw shaft, a first resilient member that engages the screw shaft to inhibit movement of the screw shaft, and a first shaft projection that engages the engager ring so that rotation of the driver shaft results in rotation of the bone screw; and a bone screw including a screw threaded region and a screw engagement region, the screw engagement region including a screw shaft and an engager ring; wherein the screw engagement region is in snap-off engagement with the screw threaded region in which the screw engagement region breaks away from the screw threaded region after the screw threaded region has been threaded into bone; wherein the first resilient member cantilevers into the shaft aperture to contact the screw shaft.

2. The bone screw driver of claim 1 wherein the driver shaft includes a second resilient member that extends into the shaft aperture to contact the screw shaft.

3. The bone screw driver of claim 2 wherein the driver shaft includes a second shaft projection and a third shaft projection that engage the engager ring so that rotation of the driver shaft results in rotation of the bone screw.

4. The bone screw driver of claim 1 wherein the driver shaft includes a second shaft projection and a third shaft projection that engage the engager ring so that rotation of the driver shaft results in rotation of the bone screw.

5. A combination comprising:
a bone screw adapted for insertion into a bone region, the bone screw including a screw threaded region and a screw engagement region, the screw engagement region including a screw shaft and an engager ring; and
a bone screw driver for inserting the bone screw into the bone region, the bone screw driver including a driver shaft having a shaft aperture for receiving at least a portion of the screw shaft, a first resilient member that engages the screw shaft to inhibit movement of the screw shaft, and a first shaft projection that engages the engager ring so that rotation of the driver shaft results in rotation of the bone screw; wherein the screw engagement region is in snap-off engagement with the screw threaded region in which the screw engagement region breaks away from the screw threaded region after the screw threaded region has been threaded into bone; wherein the first resilient member cantilevers into the shaft aperture to contact the screw shaft.

6. The combination of claim 5 wherein the driver shaft includes a second resilient member that extends into the shaft aperture to contact the screw shaft.

7. The combination of claim 6 wherein the driver shaft includes a second shaft projection and a third shaft projection that engage the engager ring so that rotation of the driver shaft results in rotation of the bone screw.

8. The combination of claim 5 wherein the driver shaft includes a second shaft projection and a third shaft projection that engage the engager ring so that rotation of the driver shaft results in rotation of the bone screw.

9. The combination of claim 5 further comprising a screw retainer that selectively retains the bone screw with the screw engagement region exposed.

10. A combination comprising:
a bone screw adapted for insertion into a bone region, the bone screw including a screw threaded region and a screw engagement region, the screw engagement region in snap-off engagement with the screw threaded region in which the screw engagement region breaks away from the screw threaded region after the screw threaded region has been threaded into bone, the screw engagement region including a screw shaft and an engager ring; and
a bone screw driver for inserting the bone screw into the bone region, the bone screw driver including a driver shaft having a shaft aperture for receiving at least a portion of the screw shaft, a first resilient member that engages the screw shaft to inhibit movement of the screw shaft, and a first shaft projection that engages the engager ring so that rotation of the driver shaft results in rotation of the bone screw; wherein the first resilient member cantilevers into the shaft aperture to contact the screw shaft.

* * * * *